United States Patent

Darby, II et al.

(10) Patent No.: US 8,900,171 B2
(45) Date of Patent: Dec. 2, 2014

(54) ADJUSTABLE SPLINTING DEVICE

(75) Inventors: H. Darrel Darby, II, Huntington, WV (US); Wu Zhang, Proctorville, OH (US)

(73) Assignee: Darco International, Inc., Huntington, WV (US)

(\*) Notice: Subject to any disclaimer, the term of this patent is extended or adjusted under 35 U.S.C. 154(b) by 384 days.

(21) Appl. No.: 12/758,518

(22) Filed: Apr. 12, 2010

(65) Prior Publication Data

US 2010/0324461 A1  Dec. 23, 2010

Related U.S. Application Data (60) Provisional application No. 61/187,852, filed on Jun. 17, 2009.

(51) Int. Cl.
*A61F 5/00* (2006.01)

(52) U.S. Cl.
USPC .................................. 602/16; 602/23; 602/27

(58) Field of Classification Search
USPC .............................. 602/5, 16, 23–28; 128/882
See application file for complete search history.

(56) References Cited

U.S. PATENT DOCUMENTS

| | | | | |
|---|---|---|---|---|
| 2,439,100 A * | 4/1948 | Richards | ......................... | 602/28 |
| 2,536,454 A * | 1/1951 | McIntyre | ........................ | 602/28 |
| 3,732,861 A * | 5/1973 | Lehneis | ........................... | 602/16 |
| 3,804,085 A * | 4/1974 | Eshuis et al. | ..................... | 602/28 |
| 4,559,934 A * | 12/1985 | Philipp | ........................... | 602/27 |
| 5,277,699 A * | 1/1994 | Williamson | .................... | 602/28 |
| 5,496,263 A * | 3/1996 | Fuller et al. | ..................... | 602/27 |
| 5,718,673 A * | 2/1998 | Shipstead | ........................ | 602/27 |
| 6,267,742 B1 * | 7/2001 | Krivosha et al. | ............... | 602/28 |
| 7,674,212 B2 * | 3/2010 | Kruijsen et al. | .............. | 482/124 |
| 7,806,844 B2 * | 10/2010 | Outred et al. | ................... | 602/28 |
| 7,828,758 B2 | 11/2010 | Clements et al. | | |
| 7,918,813 B2 | 4/2011 | Drake et al. | | |

\* cited by examiner

*Primary Examiner* — Michael A. Brown
(74) *Attorney, Agent, or Firm* — Sughrue Mion, PLLC (57) ABSTRACT

A splinting device includes a first part for contacting a lower leg and a second part for contacting a foot hingedly connected to the first part. An adjustable attachment includes an elastic part and interconnects the first part and the second part. A method of treating plantar fasciitis includes securing the first part of the splint device to the lower leg, and securing the second part to a foot. The first part is rotated relative to the second part to establish a predetermined angle between the first part and the second part. The elastic part of the adjustable attachment, which is attached to one of the first and second parts, is stretched and attached to the other of the first part of the second part at a position based on the predetermined angle to limit movement of the first part relative to the second part beyond the predetermined angle.

40 Claims, 8 Drawing Sheets

ADJUSTABLE SPLINTING DEVICE

CROSS-REFERENCE TO RELATED APPLICATION

This application claims priority from U.S. Provisional Patent Application No. 61/187,852, filed on Jun. 17, 2009, in the U.S. Patent & Trademark Office, the disclosure of which is incorporated by reference in its entirety.

BACKGROUND AND RELATED ART

1. Field of the Invention

Illustrative, non-limiting embodiments of the present invention relate generally to splinting devices, and more particularly to splinting devices for the ankle and lower leg.

2. Background of the Invention

Plantar fasciitis is a painful condition affecting the bottom of the foot. It is a common cause of heel pain and is sometimes called heel spur. A night splint can be worn while you sleep. The night splint keeps your foot from bending downward, and it places a mild stretch on the calf muscles and the plantar fascia. People seem to get better more quickly when using a night splint and they report having less heel pain when placing their sore foot on the ground in the morning.

SUMMARY OF THE INVENTION

The splinting device includes a shell include a first part and a second part hingedly connected to the first part. A strap is connected to one of the first and second parts and the other of the first and second parts includes a plurality of attachments. The other end of the strap is removably attachable to each of the attachments.

The present invention provides a dorsiflexion stretch to help relieve symptoms of plantar fasciitis or provide a low load stretch to the Achilles tendon and calf muscles after post-op immobilization. The present invention allows patients to begin with a gradual stretch and progress as the condition improves and compliance is increased. The degree of stretch can be controlled to provide a tolerable stretch force all night. The device allows a patient to easily gauge and monitor progress. The device enhances safety and comfort during nighttime ambulation due to the articulating foot piece and soft bottom.

BRIEF DESCRIPTION OF THE DRAWINGS

Features and advantages of illustrative, non-limiting embodiments of the present invention will become more apparent from a reading of the following description. The accompanying drawings, which are incorporated in and constitute a part of this specification, illustrate exemplary embodiments of the invention and, together with the description, serve to explain the aspects, advantages and principles of the embodiments. In the drawings.

DETAILED DESCRIPTION OF EXEMPLARY EMBODIMENTS OF THE INVENTION

Illustrative, non-limiting embodiments of the present invention will now be described more fully with reference to the accompanying drawings.

Figure 1:
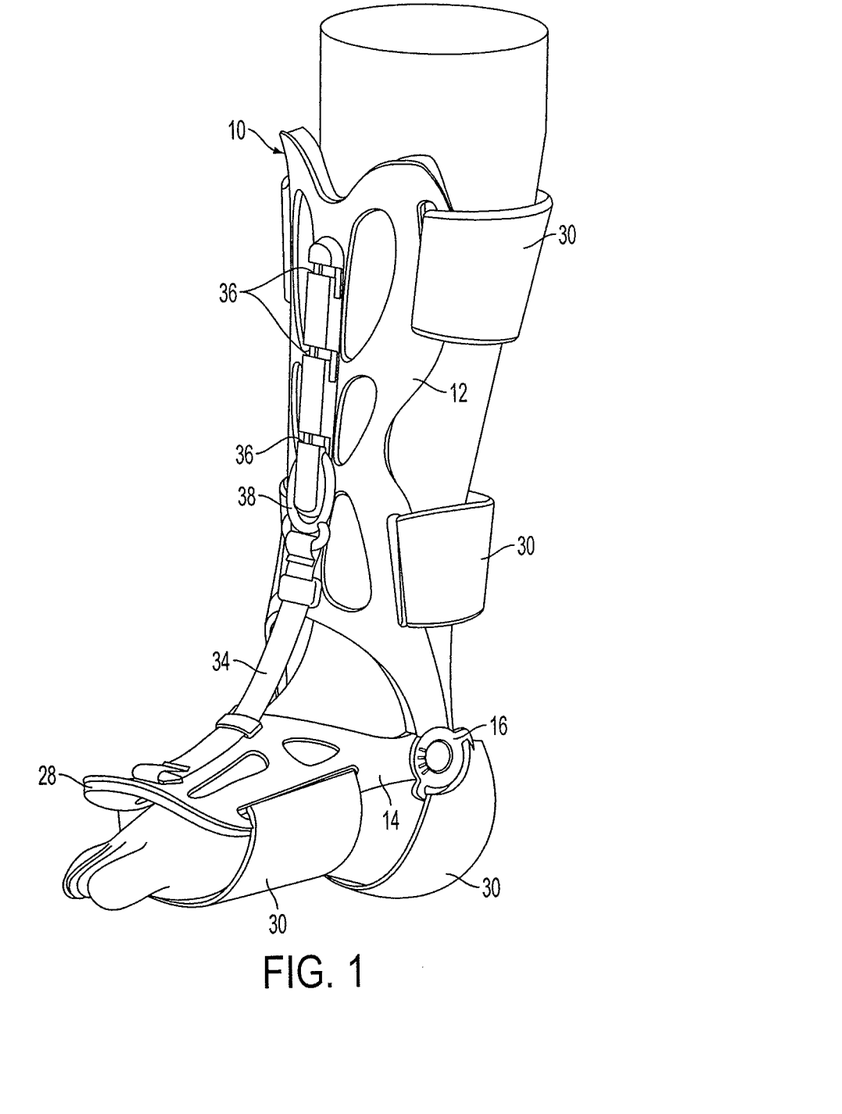
FIG. 1 is a perspective view of an embodiment of the device illustrated on a user.
Figure 2:
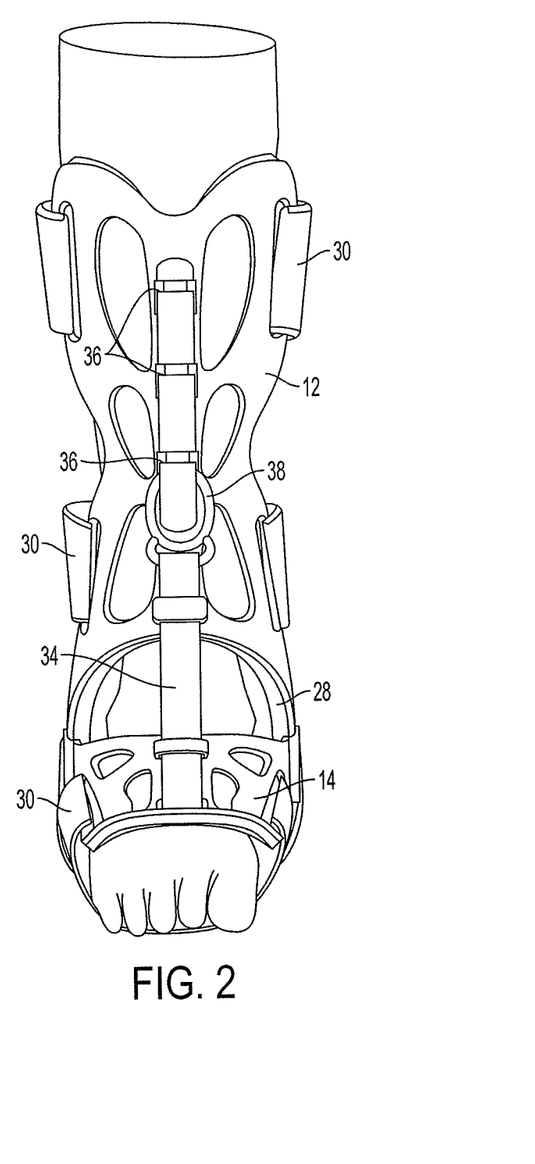
FIG. 2 is a front view of the device of FIG. 1.
Figure 3:
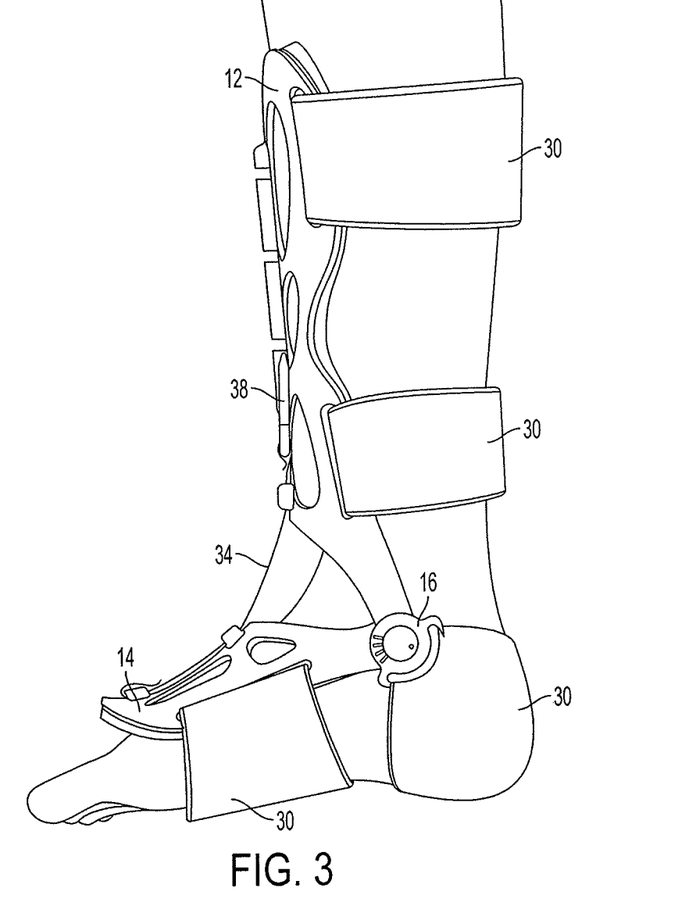
FIG. 3 is a side view of the device of FIGS. 1 and 2.
Figure 4:
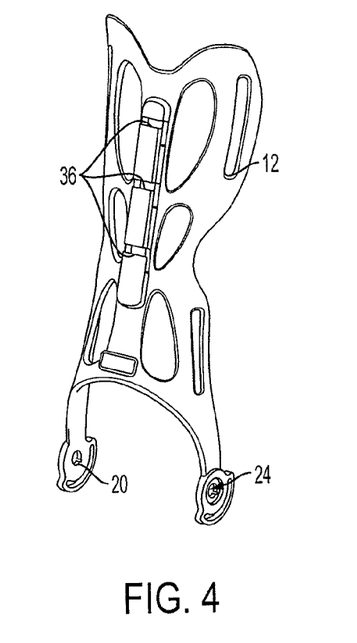
FIG. 4 is a perspective view of an embodiment of the first part of the shell.
Figure 5:
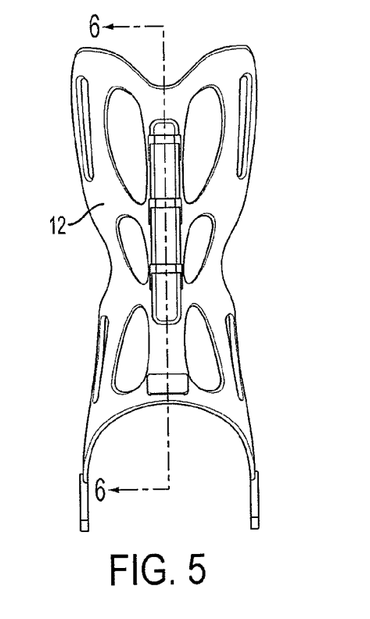
FIG. 5 is a front view of the first part of FIG. 4.
Figure 6:
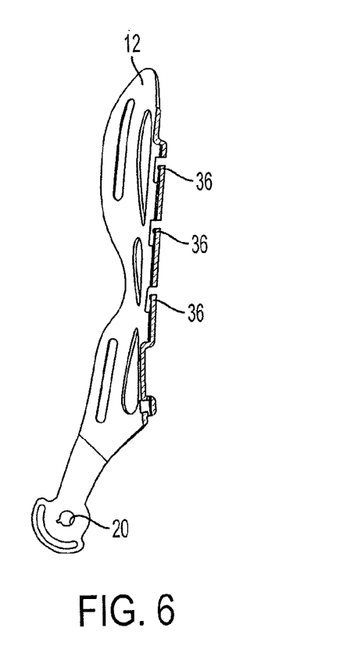
FIG. 6 is a side view in cross section of the first part of FIGS. 4 and 5 taken at line A-A in FIG. 5.
Figure 7:
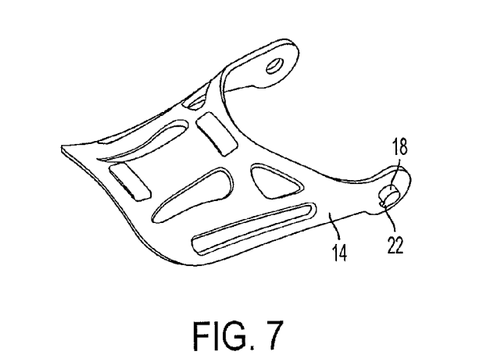
FIG. 7 is a perspective view of an embodiment of a second part of the shell.
Figure 8:
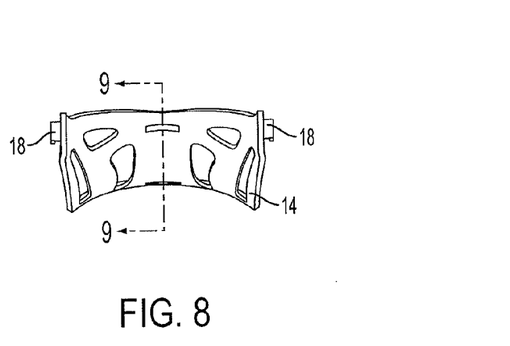
FIG. 8 is a rear view of the second part of FIG. 7.
Figure 9:
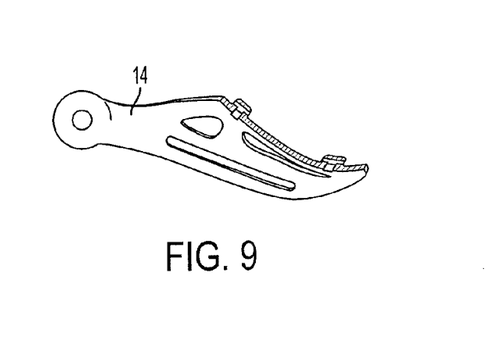
FIG. 9 is a side view in cross section of the second part of FIGS. 7 and 8 taken at line B-B of FIG. 8.
Figure 12:
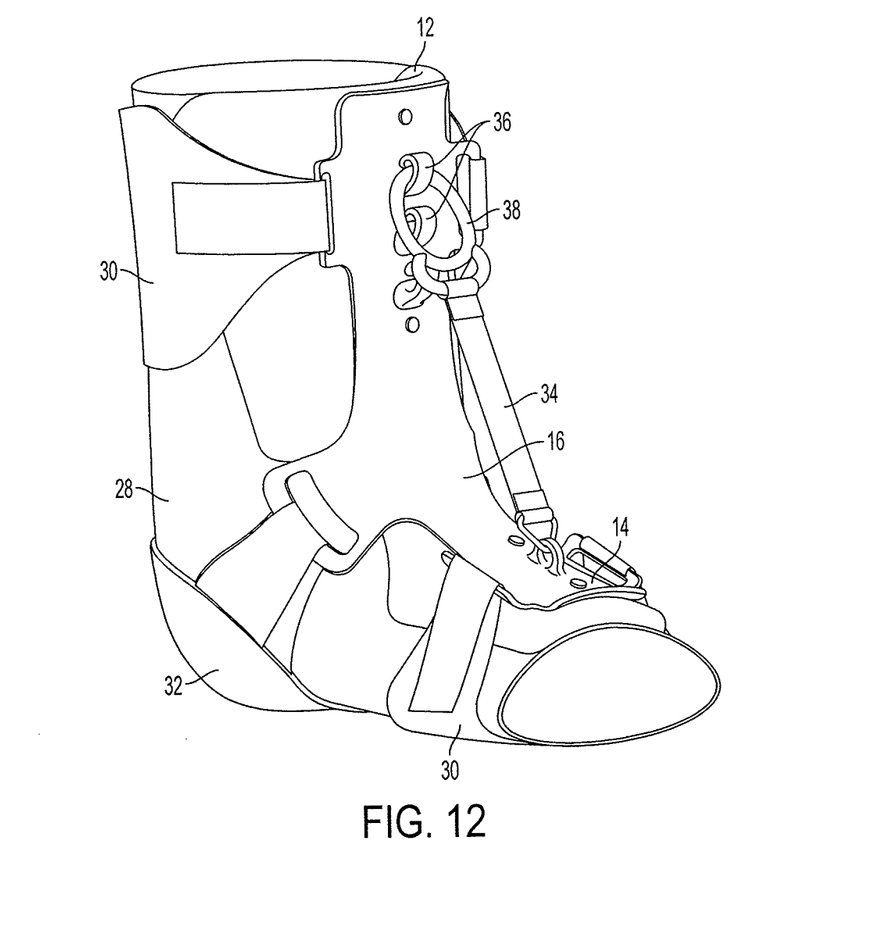
FIG. 12 is a perspective view of an alternative embodiment of the device.
Figure 13:
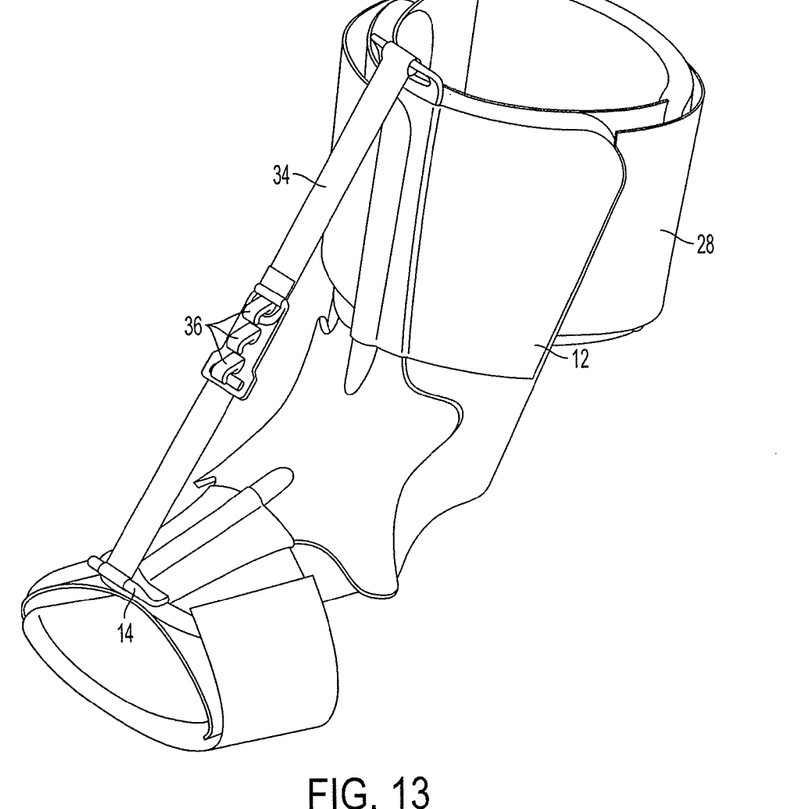
FIG. 13 is a perspective view of an alternative embodiment of the device.

The splinting device includes a dorsal shell 10 having a first upper part 12 that extends along a shin, i.e., the tibial bone, of a user and a second foot part 14 that extends along the top of the foot, i.e., the cuneiform bone, of a user, as illustrated in FIGS. 1-3. In one exemplary embodiment, the first part 12 and the second part 14 may be one integral shell that is flexible at the location 16 where the first part 12 meets the second part 14, as shown in FIGS. 12 and 13. The first part 12 and the second part 14 may be two separate pieces rotatably or pivotally connected to one another at two pivot points or hinges 16, as shown in FIGS. 1-10.

Figure 10:
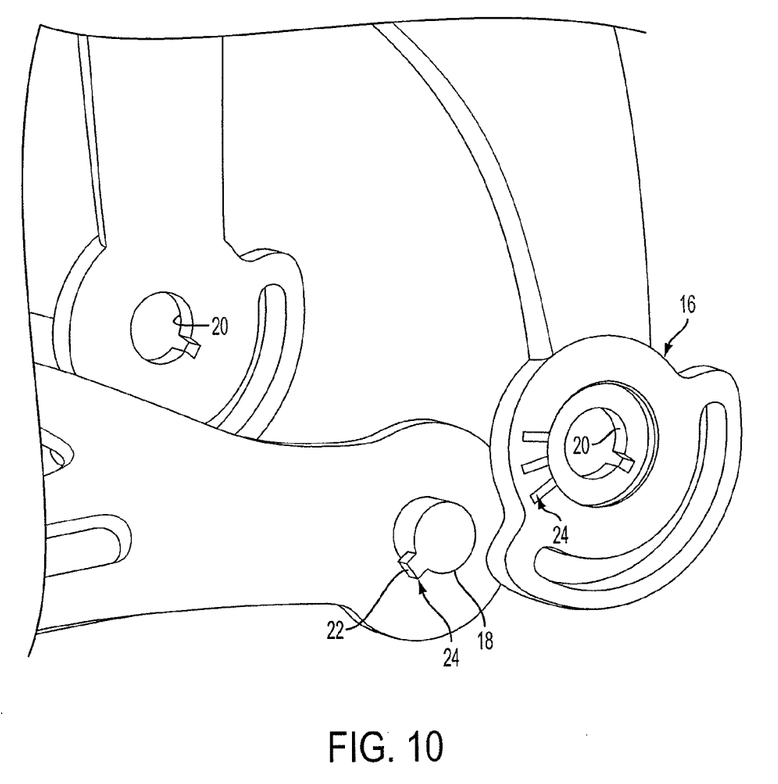
FIG. 10 is a partial perspective view of the hinge shown in FIG. 1 illustrating an embodiment of an indicator.

Each of the hinges 16 is located at one side of the ankle of the user. The hinge 16 includes a projection 18 on one of the first part 12 and the second part 14, and a through hole 20 that matches the other periphery of the projection 18 on the other of the first part 12 and the second part 14, as best illustrated in FIG. 10. The projection 18 includes a tooth 22 extending radially outwardly from a center axis of the projection 18 and adjacent the top surface of the projection 18. The tooth 22 is positioned such that the first part 12 is connected to the second part 14 at an angle that is more than 180 degrees. In other words the first part 12 is connected to the second part 14 in a position wherein the foot and leg of a user cannot be arranged relative to one another.

The hinge 16 includes a range of motion indicator 24. The indicator 24 is formed by the tooth 22 of the projection 18 being colored a different color than that of the outer surface of the part having the through hole 20 and the outer surface of the part having the through hole 20 includes indicia along the circumference of the through hole 20 as shown in the FIG. 10. By this arrangement, as the first part 12 and second part 14 are rotated relative to the one another, the tooth 22 aligns with one part of the indicia to give the user a simple and easy indication of in which position the splint is located.

A padded cloth liner 28 is disposed on the inner side of the shell 10 to abut the user's skin, as best shown in FIG. 13. The liner 28 wicks moisture, promoting dry skin and comfortable wear.

A plurality of straps 30 connect the first part 12 to the leg of the user and the second part 14 to the foot of the user. The straps 30 may be cloth which contours to fit the leg and calf. One of the straps 30 may be located at the heel of a user and includes a heel plate 32 which secures the device on the foot and prevent the splint from sliding off the foot.

Figure 11:
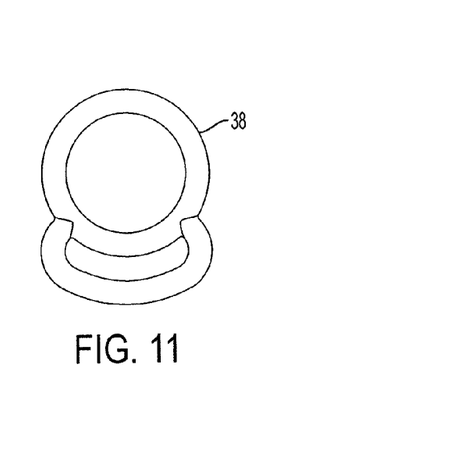
FIG. 11 is a front view of an embodiment of an elastic part.

An adjustment strap 34 is connected to one of first part 12 and the second part 14. The other of the first part 12 and the second part 14 includes a plurality of attachments 36. The attachments 36 may be disposed along the other of the first part 12 and second part 14 and spaced from one another, as shown in the embodiments of FIGS. 1-3 and 12. Alternatively, the attachments 16 may be disposed along a strap connected to the other of the first part 12 and second part 14, as shown in FIG. 13. An elastic part 38 is connected to the other end of the adjustment strap 34 and removably attaches to one of the attachments 36. The attachments 36 may be hooks. As shown in FIG. 11, the elastic part 38 may be a dynamic elastic ring. The figures illustrate three attachments 36 on the first part 12 of the splinting device, however the attachments may be provided on the second part 14 and there may be a different number of attachments 36. Furthermore, as shown in at least FIG. 1, the adjustment strap 34 is positioned entirely on an exterior side of both of the first part 12 and the second part 14.

The location of the attachments 36, the length of the adjustment strap 34, and the location where the end of the adjustment strap 34 connects to one of the first part 12 and second 14 establishes predetermined angles of the first part 12 relative to the second part 14. The angles for example may be 90 degrees, 85 degrees, and 80 degrees. By this arrangement, the user can flex and stretch the elastic part 38 onto one of the attachments 36 and once in place, the first part 12 is limited from movement beyond a predetermined angle relative to the second part 14 and the user's foot remains in a stretched position the extent of which is set by the predetermined angle.

Although the invention has been explained in relation to certain exemplary and preferred embodiments, it is to be understood that many other possible modifications and variations can be made without departing from the spirit and scope of the invention as hereinafter claimed.

What is claimed is:

1. A therapeutic device comprising:
   an upper portion constructed to contact a lower leg;
   a foot portion constructed to contact a foot and be integral with the upper portion,
   a tensioning element that directly connects a forward portion of said foot portion to said upper portion at a connection point on said upper portion to permit adjustment of a relative angle between said foot portion and said upper portion, and
   an interconnecting pivoting part being separate from the tensioning element and integrally and directly connecting the upper portion to the foot portion,
   wherein said tensioning element is positioned entirely on an exterior side of both of said upper portion and said foot portion, and
   said connection point on said upper portion is positioned above said interconnecting pivoting part.

2. The device of claim 1, wherein the upper portion is substantially rigid.

3. The device of claim 1, wherein the foot portion is substantially rigid.

4. The device of claim 1, wherein the foot portion includes a toe anchor to which the tensioning element is attached.

5. The device of claim 1, further comprising a lower leg strap connected to said upper portion and constructed to be wrapped about the lower leg, wherein the lower leg strap is stretchable.

6. The device of claim 5, wherein the lower leg strap comprises a plurality of fabric hook and loop fasteners.

7. The device of claim 1, further comprising a foot strap connected to said foot portion and constructed to be wrapped about a foot, wherein the foot strap is stretchable.

8. The device of claim 7, wherein the foot strap comprises a plurality of fabric hook and loop fasteners.

9. The device of claim 1, wherein the tensioning element comprises a shock cord.

10. The device of claim 1, wherein the upper portion includes an anchor to which the tensioning element is attached.

11. The device of claim 1, wherein the tensioning element comprises a single elastic cord.

12. The device of claim 1, wherein said foot portion is pivotally connected to said upper portion at a pivot point.

13. The device of claim 12, wherein the pivot point includes a range of motion indicator.

14. The device of claim 1, wherein said foot portion and said upper portion form an L-shape having a vertex and the interconnecting pivoting part connects the foot portion and the vertex.

15. A therapeutic device comprising:
    an upper portion;
    a foot portion pivotally connected to said upper portion at a pivot point;
    a lower leg strap connected to said upper portion and constructed to be wrapped about a leg;
    a foot strap connected to said foot portion and constructed to be wrapped about a foot; and
    a single shock cord extending between spaced, confronting locations on said upper portion and said foot portion, the locations being spaced from said pivot point,
    wherein said shock cord is positioned entirely on an exterior side of both of said upper portion and said foot portion.

16. The device of claim 15, wherein the upper portion is disposed adjacent a tibial bone.

17. The device of claim 15, wherein the foot portion is disposed adjacent a cuneiform bone.

18. A method for treating plantar fasciitis comprising:
    providing a splint device having an upper portion, a foot portion and an elastic tensioning element, the upper portion and foot portion being pivotally disposed with respect to one another at a pivot point;
    detaching the elastic tensioning element from one of the upper portion and the foot portion;
    pivoting the upper portion with respect to the foot portion;
    securing the upper portion of the splint device to a lower leg adjacent a tibial bone;
    securing the foot portion to an upper surface of a foot adjacent a cuneiform bone;
    urging the foot portion and upper portion together with the elastic tensioning element which extends between the foot portion and the upper portion; and
    providing a desired tension on the elastic tensioning element by selecting a desired point of attachment on the elastic tensioning device to at least one of the upper portion and the foot portion,
    wherein the elastic tensioning element is positioned entirely on an exterior side of both of said upper portion and said foot portion.

19. The method of claim 18, further comprising providing a range of motion indicator on the pivot point.

20. The method of claim 18, wherein securing the upper portion of the splint device to the lower leg comprises strapping the splint device to a calf region.

21. The method of claim 18, wherein securing the foot portion of the splint device to the upper surface of the foot comprises strapping the splint to the foot.

22. The method of claim 18, further comprising adjusting a length of the elastic tensioning element between the foot portion and the upper portion.

23. The method of claim 22, wherein adjusting a length of the elastic tensioning element comprises:

disengaging the tensioning element from one of the foot portion and the upper portion at a first pint of attachment;
selecting a desired length of the elastic tensioning element;
re-attaching the elastic tensioning element to the one of the foot portion and the upper portion at a second point of attachment on the elastic tensioning element different from the first point.

24. The method of claim 18, further comprising adjusting tension on the elastic tensioning element by selecting a point on the elastic tensioning element which is attached to one of the upper portion and the foot portion for a fixed angle between the upper portion and the foot portion.

25. The method of claim 16, further comprising adjusting tension on the elastic tensioning element by adjusting an angle formed between the upper portion and the foot portion while the elastic tensioning element remains attached to the foot portion and the upper portion.

26. A splinting device comprising:
a first part for contacting a lower leg of a user and a second part for contacting a foot of the user and being integral with the first part;
an adjustable attachment that directly connects the first part to a forward portion of the second part at a connection point on said first part to permit adjustment of a relative angle between the first part and the second part, and
an interconnecting pivoting part being separate from the tensioning element and integrally and directly connecting the upper portion to the foot portion,
wherein the adjustable attachment is positioned entirely on an exterior side of both of the first part and the second part, and
said connection point on said first part is positioned above said interconnecting pivoting part.

27. The device of claim 26, wherein one end of the adjustable attachment is connected to the second part, and another end of the adjustable attachment is detachably connected to the first part.

28. The device of claim 26, wherein the second part is hingedly connected to the first part at a location.

29. The device of claim 28, wherein the location includes an indicator.

30. The device of claim 26, wherein the adjustable attachment comprises an elastic part.

31. The device of claim 30, wherein the elastic part is a dynamic elastic ring.

32. A splinting device comprising:
a first part;
a second part hingedly connected to said first part at a location;
a lower leg strap connected to said first part for securing the first part to a leg;
a foot strap connected to said second part for securing the second part to a foot; and
an adjustment strap including an elastic part, the adjustment strap extending between said first part and said second part,
wherein the adjustable strap is positioned entirely on an exterior side of both of the first part and the second part.

33. The device of claim 32, further comprising a plurality of attachments disposed on at least one of the first part, the second part, and the adjustment strap, wherein the attachments are spaced from one another.

34. The device of claim 32, wherein the first part is disposed adjacent the leg.

35. The device of claim 34, wherein the second part is disposed adjacent the foot.

36. A method for treating plantar fasciitis comprising:
providing a splint device having a first part, a second part and an adjustable attachment including an elastic part, the first part and the second part being hingedly disposed with respect to one another at a location, and the adjustable attachment being connected to one of the first part and the second part;
securing the first part of the splint device to a lower leg;
securing the second part of the splint device to a foot;
rotating the first part relative to the second part;
establishing a predetermined angle between the first part and the second part;
stretching the elastic part of the adjustable attachment;
attaching the elastic part to another of the first part of the second part at a position based on the predetermined angle to limit movement of the first part relative to the second part beyond the predetermined angle,
wherein the adjustable attachment and the elastic part are positioned entirely on an exterior side of both of the first part and the second part.

37. The method of claim 36, further comprising providing an indicator on the location between the first part and the second part.

38. The method of claim 36, wherein securing the first part of the splint device to the lower leg comprises strapping the splint device to a calf region.

39. The method of claim 36, wherein securing the second part of the splint device to the foot comprises strapping the splint to the foot.

40. A therapeutic device comprising:
an upper portion constructed to contact a lower leg;
a foot portion constructed to contact a foot and be integral with the upper portion,
a tensioning element that directly connects a forward portion of said foot portion to said upper portion to permit adjustment of a relative angle between said foot portion and said upper portion, and
an interconnecting pivoting part being separate from the tensioning element and integrally and directly the upper portion to the foot portion,
wherein said tensioning element includes a strap with a connector connected to said upper portion,
said connection point on said first part is positioned above said interconnecting pivoting part.

* * * * *